United States Patent [19]
Plunkett et al.

[11] Patent Number: 5,741,424
[45] Date of Patent: Apr. 21, 1998

[54] METHOD OF FACILITATING OXYGEN TRANSPORT IN BLOOD OXYGENATORS

[75] Inventors: Sean D. Plunkett, Mission Viejo; Henry W. Palermo, Burbank, both of Calif.

[73] Assignee: Medtronic, Inc., Minneapolis, Minn.

[21] Appl. No.: 643,146

[22] Filed: Apr. 30, 1996

[51] Int. Cl.$^6$ .............................. A61M 1/14; A61M 1/16; B01D 61/00
[52] U.S. Cl. ........................ 210/644; 210/640; 210/645; 422/45; 422/48
[58] Field of Search ................................... 210/640, 644, 210/645; 422/45, 48

[56] References Cited

U.S. PATENT DOCUMENTS

| | | | |
|---|---|---|---|
| 4,609,383 | 9/1986 | Bonaventura et al. | 210/640 |
| 5,277,176 | 1/1994 | Habashi et al. | 128/200.24 |

*Primary Examiner*—John Kim
*Attorney, Agent, or Firm*—Harry G. Weissenberger

[57] ABSTRACT

Oxygen transfer to blood plasma in a blood oxygenator using a microporous membrane exposed to blood on one side and to oxygen on the other is facilitated by bonding an oxygen-carrying chemical such as hematin or a perfluorocarbon to at least the blood-contacting surface of the membrane.

7 Claims, 3 Drawing Sheets ts at which the blood plasma is exposed to essentially
5,741,424

METHOD OF FACILITATING OXYGEN TRANSPORT IN BLOOD OXYGENATORS

FIELD OF THE INVENTION

This invention relates to blood oxygenators, and more particularly to a method of increasing the oxygen flux to the blood by surface-modifying the oxygen-transferring membrane or fiber with oxygen-carrying chemicals so as to enhance its ability to transport oxygen.

BACKGROUND OF THE INVENTION

Blood oxygenators are in common use in the heart-lung machines which take the place of the heart and lungs during open heart surgery. In these oxygenators, blood is brought into contact with one side of microporous membranes or hollow fibers (hereafter collectively referred to as membranes). Oxygen is conveyed along the other side of the membrane, and a gas exchange takes place through the membrane wall in which oxygen enters the blood, and carbon dioxide is removed from the blood.

The membrane is made from a microporous material, so that the blood-gas interface consists of a multitude of fine pores at which the blood plasma is exposed to essentially pure oxygen. There are several reasons why it is desirable to reduce the size of the oxygenator. For one, the microporous material is expensive, so that a reduction in the amount of membrane material reduces cost; secondly, the microporous material is a foreign substance, and less exposure of the blood to it reduces blood trauma and whole-body inflammatory response; and thirdly, a smaller oxygenator requires less blood priming volume. However, any size reduction is limited by the fact that at the transfer rate or flux of about 0.250 g/m²/min, which is currently the state of the art in commercial oxygenators, a membrane surface of about 2 m² is required to maintain hemostasis in adults during a cardiopulmonary bypass procedure.

This is so because in the operation of an oxygenator, the blood plasma which carries the red blood cells (RBCs) is exposed to gaseous oxygen at the blood-gas interface in the pores of the microporous membrane material. The gaseous oxygen is dissolved into the plasma by normal gas-liquid diffusion. At the same time, RBCs absorb dissolved oxygen from the plasma. The rate at which oxygen moves from the gas phase, through the plasma and into RBCs is controlled by the dynamic equilibrium that is established in the system. This rate depends on a number of factors including the concentration of oxygen in the gas phase, the interfacial surface area between the gas and liquid phases, the temperature of the system, the solubility of oxygen in plasma (i.e. water), the rate of oxygen uptake by RBCs and the flow rate of the blood.

Typically, the amount of oxygen available for transfer to RBCs at any given moment depends on the solubility (i.e. saturation level) of oxygen on the blood side of the microporous membrane. The solubility of $O_2$ at physiological temperatures is about 7 mg/liter. As blood passes through an oxygenator, it needs to pick up about 100 mg/liter of oxygen. This quantity of oxygen is supplied exclusively by transfer from the gas phase through the plasma, and the solubility of oxygen in plasma is a given. Thus, the amount of oxygen available per unit area on the blood side of the membrane is a limiting factor in the size reduction of a blood oxygenator.

SUMMARY OF THE INVENTION

The present invention increases the ability of the membrane material to transport oxygen by increasing the local concentration of oxygen on the blood side of the material. This is achieved, in accordance with the invention, by chemically modifying the surface of the material with an oxygen carrier to increase its affinity to oxygen. Such a surface modification can be produced by a variety of known processes which allow heme-type molecules (e.g. iron-containing porphines such as hematin and perfluorocarbons) to be bonded to the surface of the microporous material. In a preferred embodiment, the modification would be done only on the blood contacting surface of the membrane, but it can advantageously also be done on the gas side and/or the body of the membrane.

An additional advantage of providing a surface carrier is that it also increases the diffusion across the gas-liquid interface by transporting more oxygen between pores along the blood-contacting surface of the membrane. Such surface diffusion in a bonded layer increases the flux by providing an additional pathway for oxygen transport.

DESCRIPTION OF THE PREFERRED EMBODIMENT

Figure 1:
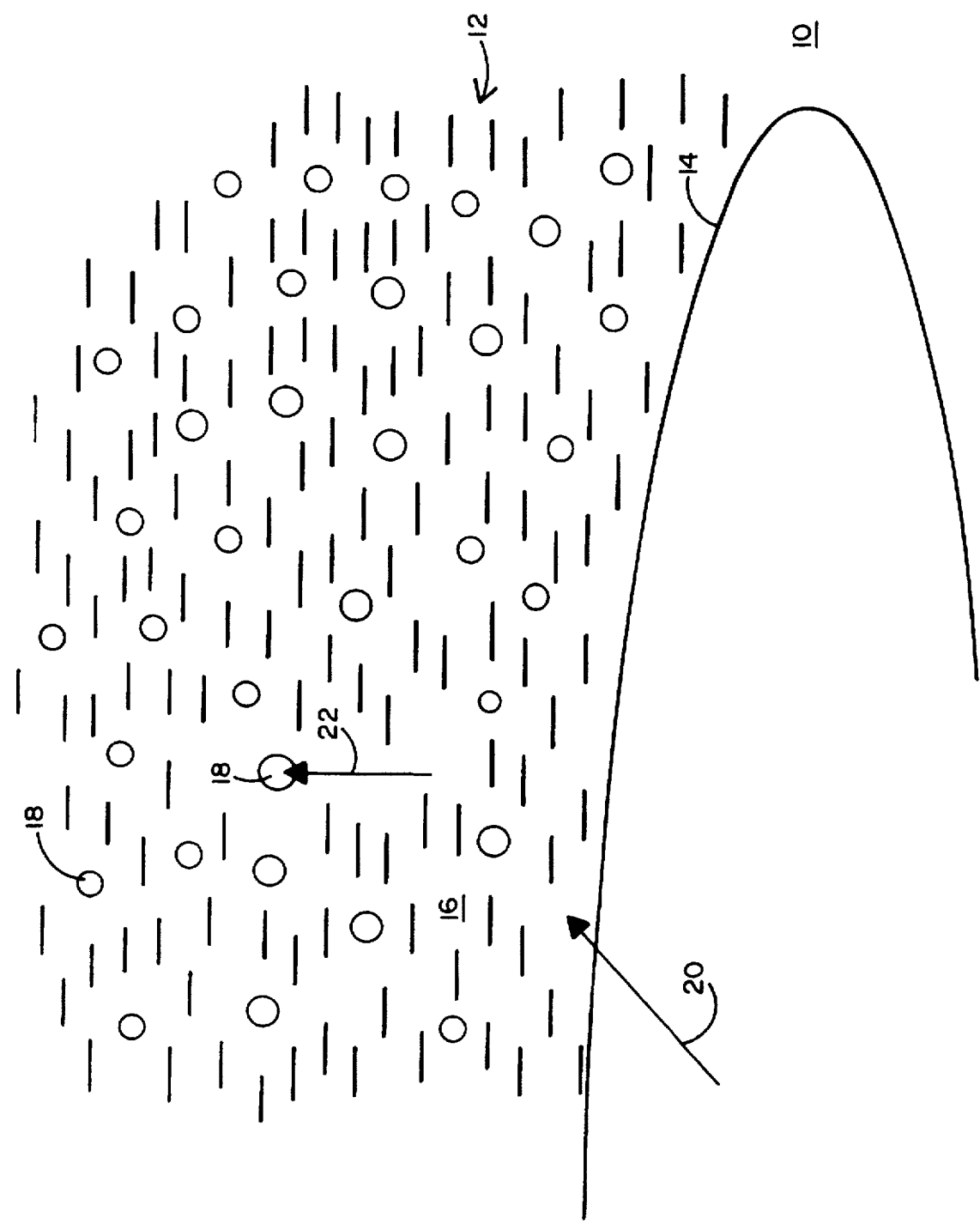
FIG. 1 is a schematic view of a conventional transfer of oxygen through a microporous membrane.

As illustrated schematically in FIG. 1, oxygen in a conventional microporous membrane 10 enters the blood stream 12 through a pore 14. The blood stream 12 consists of blood plasma 16 which carries red blood cells 18. (The RBCs 18 and the proteins which make up the blood plasma 16 are actually much larger than the pore 14 but have been drawn small to illustrate the principles involved.)

Oxygen enters the blood stream 12 through the pore 14 (arrow 20) and is dissolved in plasma 16. The RBCs 18 carried by the plasma 16 constantly absorb oxygen from the plasma solution (arrow 22) and discharge carbon dioxide into the plasma 16.

When the system is in equilibrium, the maximum free $O_2$ concentration in the plasma 16 (i.e. $O_2$ not bound to with RBCs), is about 7 mg/l. The continuous absorption of $O_2$ by the RBC's 18 reduces this concentration even further unless a plentiful supply of oxygen is constantly available for solution into the plasma 16.

In the operation of the oxygenation system, it is necessary for the RBCs flowing through the oxygenator to pick up about 100 mg/l/min of oxygen to reach the desired level of saturation. At a blood flow rate of 6 l/min, over approximately 2 m² of membrane surface this translates into a required oxygen transfer or flux rate of 0.5 g/m²/min. Although the limiting factor for the flux rate is the maximum solubility of oxygen in the plasma 16, which is a physiological given, the actual flux rate can be improved in practice by increasing the amount of oxygen available at the membrane surface for transfer to the plasma 16. This allows the free $O_2$ concentration in the plasma 16 to be continuously maintained near its physiological maximum.

Figure 2:
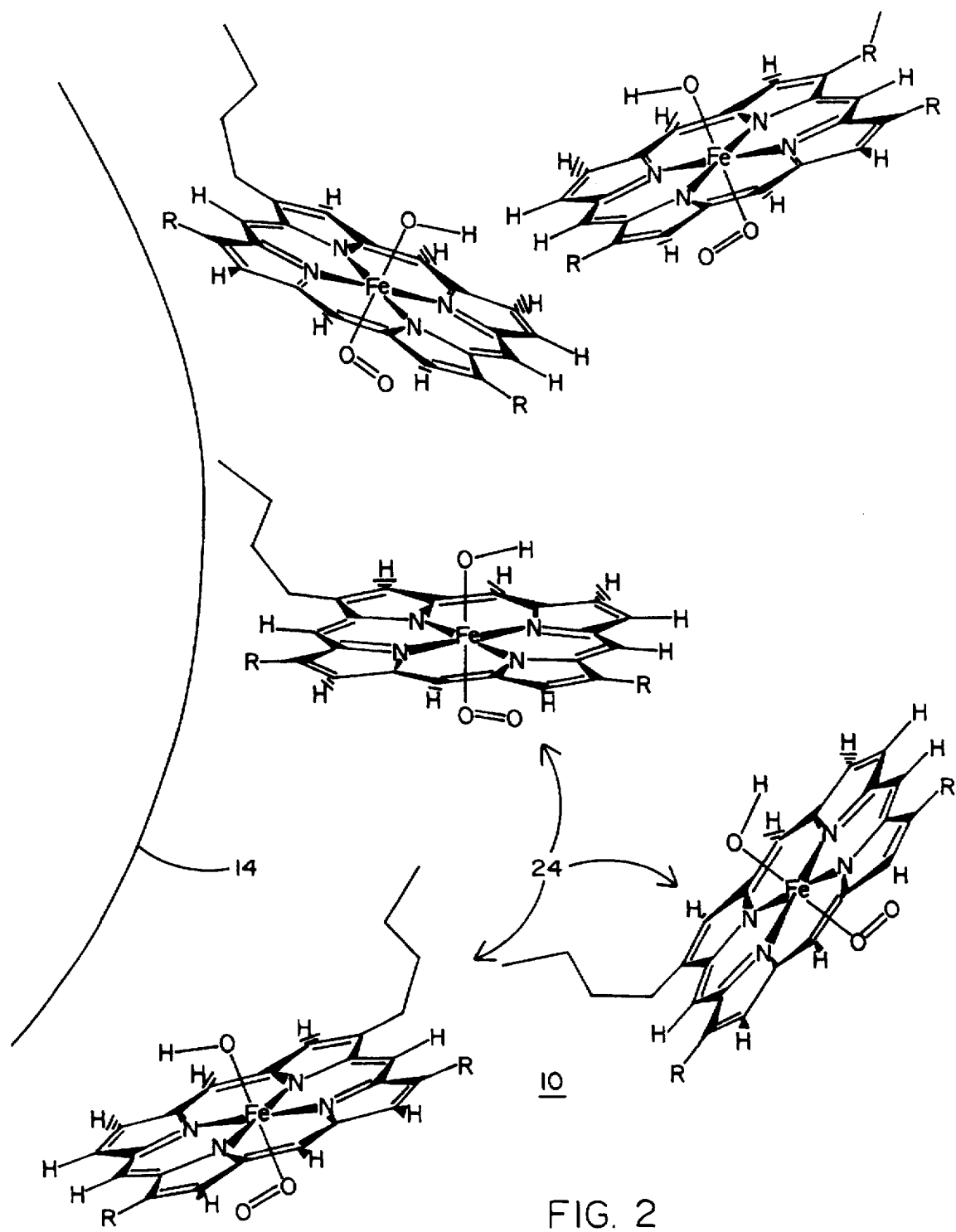
FIG. 2 is a schematic view illustrating a deposit of heme-type molecules in the pore area of a microporous membrane material according to the invention.

FIG. 2 illustrates a way of increasing the concentration of oxygen available to the plasma 16 at the blood-oxygen interface of the pore 14 in accordance with the invention. Surface-bonded oxygen carrier molecules 24 (drawn much larger than in reality) are provided on the blood-contacting surface of the microporous membrane 10 (and also, if desired, on or in its oxygen-contacting surface and/or its body) by any of several known techniques. For example, an appropriate carrier may be applied to the membrane 10 by surface grafting, vapor-phase deposition, extrusion-level blending (e.g. by a surface "bloom" process), solvent coating or adsorption coating.

Figure 3:
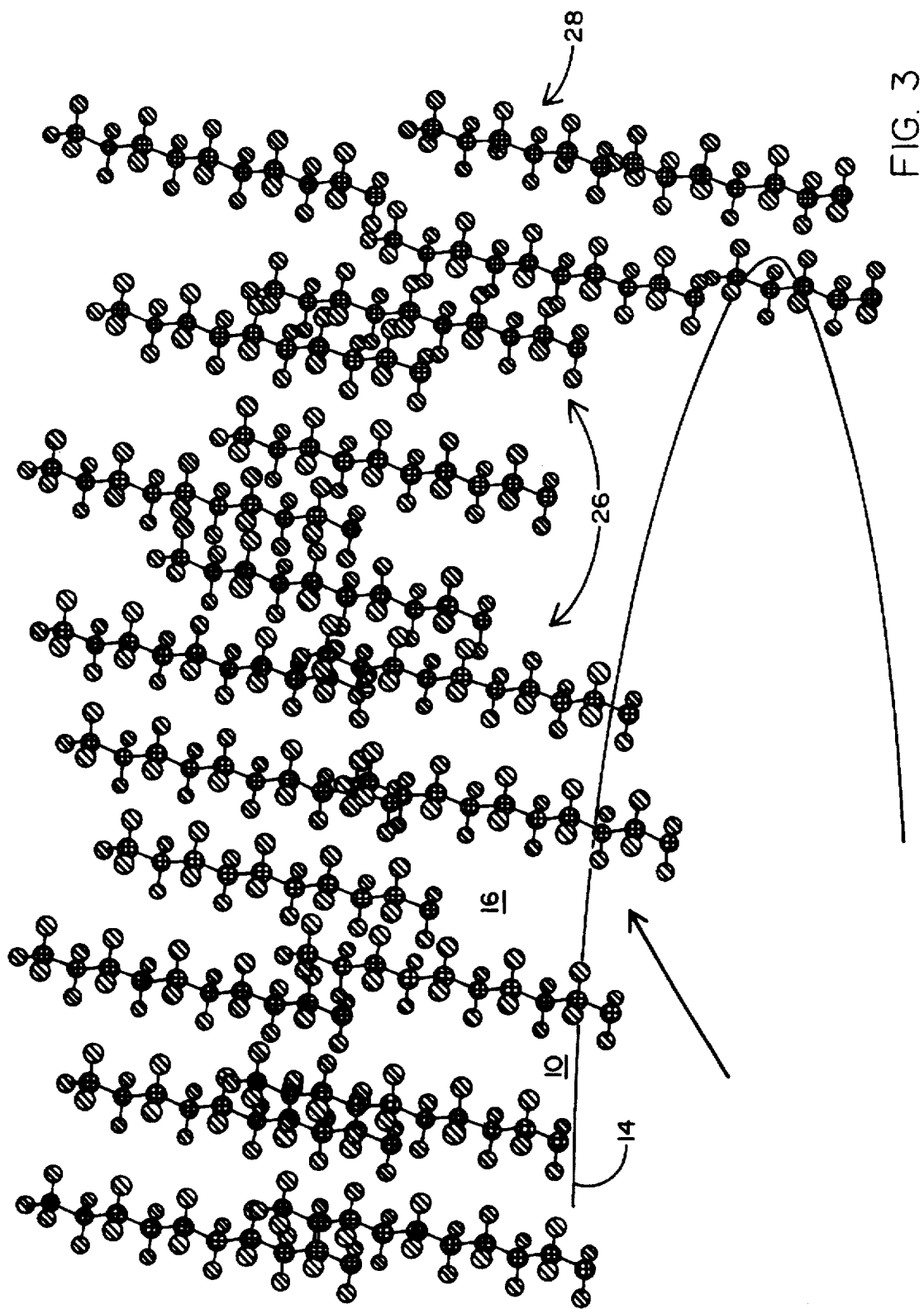
FIG. 3 is a schematic view illustrating an oxygen-diffusing membrane using a bonded fluorocarbon layer along the blood-contacting side of the microporous membrane material.

Most known chemical oxygen carriers can be used in this invention. Specifically, in a preferred embodiment of the invention, the carrier may be an iron-containing porphine such as hematin (FIG. 2) or a perfluorocarbon (FIG. 3). Inasmuch as the amount of oxygen available for transfer to the plasma 16 depends on the oxygen-carrying capacity per unit area of the blood-contacting membrane surface (a factor analogous to the solubility of oxygen in plasma, which is capacity per unit volume), the chosen carrier should have as high a capacity per unit area as possible.

As illustrated in FIG. 3 with perfluorocarbon molecules 26 (again vastly enlarged in the drawing as compared to the pore 14), diffusion across the blood-oxygen interface can further be increased by transporting more oxygen along the blood-contacting surface of the membrane 10 so as to, in effect, enlarge the interface area. This is accomplished in FIG. 3 by a layer 28 of oxygen carrier bonded to the entire blood-contacting surface of the membrane 10. The layer 28 distributes the oxygen entering through the pore 14 along the blood-contacting surface of membrane 10 and thus considerably enlarges the blood-oxygen contact area at which diffusion of oxygen into the plasma 16 can take place.

It is understood that the exemplary blood oxygenator described herein and shown in the drawings represents only a presently preferred embodiment of the invention. Indeed, various modifications and additions may be made to such embodiment without departing from the spirit and scope of the invention. Thus, other modifications and additions may be obvious to those skilled in the art and may be implemented to adapt the present invention for use in a variety of different applications.

We claim:

1. A method of facilitating oxygen transfer into blood plasma flowing along a microporous membrane whose other side is exposed to oxygen and which provides a blood-oxygen interface in a blood oxygenator, comprising the steps of:

a) bonding to the blood-contacting surface of said membrane at said interface an oxygen-carrying chemical; and b) exposing said chemical to oxygen at said interface.

2. The method of claim 1, in which said oxygen-carrying chemical is bonded as an oxygen-carrying layer to substantially the entire blood-contacting surface of said membrane.

3. The method of claim 1, in which said chemical consists essentially of iron-containing porphines.

4. The method of claim 1, in which said chemical consists essentially of perfluorocarbons.

5. The method of claim 1, in which said bonding step is carried out by a technique selected from the group consisting of surface grafting, vapor-phase deposition, extrusion-level blending, solvent coating and adsorption coating.

6. The method of claim 1, in which said oxygen-carrying chemical is also bonded to the oxygen-contacting surface of said membrane.

7. The method of claim 1, in which said oxygen-carrying chemical is also bonded to the body of said membrane.

* * * * *